(12) United States Patent
Kitamura et al.

(10) Patent No.: US 9,458,429 B2
(45) Date of Patent: Oct. 4, 2016

(54) MESENCHYMAL STEM CELL ATTRACTANT AND METHOD FOR ATTRACTING MESENCHYMAL STEM CELL

(75) Inventors: Keiko Kitamura, Kobe (JP); Yuta Inami, Kobe (JP); Koichi Nakaoji, Kobe (JP); Kazuhiko Hamada, Kobe (JP); Akito Maeda, Suita (JP); Tadashi Furumoto, Suita (JP); Yasufumi Kaneda, Suita (JP); Katsuto Tamai, Suita (JP)

(73) Assignees: Pias Corporation, Osaka (JP); Osaka University, Osaka (JP)

( * ) Notice: Subject to any disclaimer, the term of this patent is extended or adjusted under 35 U.S.C. 154(b) by 33 days.

(21) Appl. No.: 13/700,844

(22) PCT Filed: Mar. 11, 2011

(86) PCT No.: PCT/JP2011/055823
§ 371 (c)(1),
(2), (4) Date: Nov. 29, 2012

(87) PCT Pub. No.: WO2011/152100
PCT Pub. Date: Dec. 8, 2011

(65) Prior Publication Data
US 2013/0071920 A1    Mar. 21, 2013

(30) Foreign Application Priority Data
Jun. 1, 2010 (JP) .................. 2010-125905

(51) Int. Cl.
| | | |
|---|---|---|
| C12N 5/071 | (2010.01) | |
| C12N 5/0775 | (2010.01) | |
| A61K 36/47 | (2006.01) | |
| A61K 36/60 | (2006.01) | |
| A61K 36/65 | (2006.01) | |
| A61K 36/736 | (2006.01) | |
| A61K 36/74 | (2006.01) | |

(52) U.S. Cl.
CPC ............. *C12N 5/0662* (2013.01); *A61K 36/47* (2013.01); *A61K 36/60* (2013.01); *A61K 36/65* (2013.01); *A61K 36/736* (2013.01); *A61K 36/74* (2013.01)

(58) Field of Classification Search
None
See application file for complete search history.

(56) References Cited

U.S. PATENT DOCUMENTS

| 390,543 | A  | * | 10/1888 | Tomlinson .......................... 405/2 |
| 2005/0013790 | A1 | * | 1/2005 | Yamaki et al. .................. 424/74 |
| 2006/0127373 | A1 | | 6/2006 | Son et al. |
| 2007/0212676 | A1 | | 9/2007 | Takakura et al. |
| 2007/0264361 | A1 | | 11/2007 | Jo et al. |
| 2008/0206373 | A1 | * | 8/2008 | Millikin et al. .............. 424/769 |
| 2008/0254019 | A1 | | 10/2008 | Kato et al. |
| 2009/0202500 | A1 | | 8/2009 | Tamai et al. |
| 2012/0070407 | A1 | * | 3/2012 | Lazdunski et al. .......... 424/85.2 |

FOREIGN PATENT DOCUMENTS

| CN | 1570086 | A | 1/2005 |
| CN | 1935227 | A | 3/2007 |
| JP | 6329545 | A | 11/1994 |
| JP | 08-245409 | | 9/1996 |
| JP | 09-020633 | | 1/1997 |
| JP | 9157176 | A | 6/1997 |
| JP | 09-020633 | | 11/1997 |
| JP | 10-203991 | | 8/1998 |
| JP | 2000-159531 | | 6/2000 |
| JP | 2001-163794 | | 6/2001 |
| JP | 2003146837 | A | 5/2003 |
| JP | 2003261454 | A | 9/2003 |
| JP | 2006-117592 | | 5/2006 |
| JP | 2006124389 | A | 5/2006 |
| JP | 2006176480 | A | 7/2006 |
| JP | 2008511617 | A | 4/2008 |
| JP | 2009-232724 | | 10/2009 |
| JP | 2011-020974 | | 2/2011 |
| WO | 2005063967 | A1 | 7/2005 |
| WO | 2005094888 | A1 | 10/2005 |
| WO | 2007015546 | A1 | 2/2007 |
| WO | 2008053892 | A1 | 5/2008 |
| WO | WO 2008101932 | A2 * | 8/2008 |
| WO | 2009133940 | A1 | 11/2009 |

OTHER PUBLICATIONS

Mareschi et al. "Multipotent mesenchymal stem cells from amniotic fluid originate neural precursors with functional voltage-gated sodium channels", Cytotherapy 11(5): 534-547, 2009.*
Erggelet et al. "Regeneration of ovine articular cartilage defects by cell-free polymer-based implants", Biomaterial 28: 5570-80, 2007.*
Barrilleaux L. et al., Small-Molecule Antagonist of Macrophage Migration Inhibitory Factor Enhances Migratory Reponse of Mesenchymal Stem Cells to Bronchial Epithelial Cells, Tissue Engineering, Part A, 2009, vol. 15, No. 9, pp. 2335-2346.
Wang et al., MCP-1, MIP-1, IL-8 and Ischemic Cerebral Tissue Enhance Human Bone Marrow Stromal Cell Migration in Interface Culture, Hematology, 2002, vol. 7, No. 2, pp. 113-117.
The Annual Meeting of the Japanese Society of Pharmacognosy Abstract Papers. vol. 56, p. 217 (2009).
Chinese Journal of Integrative Medicine on Cardio/Cerebrovascular; Feb. 2010. vol. 8, No. 2.
Study of the Chemical Constituents of Tilia Mongolica Bark and Wood (Apr. 15, 2010).
Study of Bone Marrow Mesenchymal Stem Cells Differentiation Intervened by Traditional Chinese Medicine (Aug. 15, 2006).
Chinese Journal of Clinical Rehabilitation. Oct. 5, 2004, vol. 8, No. 28.

* cited by examiner

*Primary Examiner* — Emily Cordas
(74) *Attorney, Agent, or Firm* — Berliner Steffin Azod LLP

(57) ABSTRACT

The present invention aims to provide a mesenchymal stem cell attractant capable of attracting a mesenchymal stem cell; and others. The present invention provides a mesenchymal stem cell attractant containing at least one selected from the group consisting of an extract of a *Bodhi* tree, an extract of the root bark of *Paeonia suffruticosa Andrews*, an extract of *Mallotus philippinensis*, an extract of *Uncaria gambir* an extract of *Pashanbheda*, and an extract of a plant belonging to the genus *Prunus*.

9 Claims, 3 Drawing Sheets

MESENCHYMAL STEM CELL ATTRACTANT AND METHOD FOR ATTRACTING MESENCHYMAL STEM CELL

TECHNICAL FIELD

The present invention relates to a mesenchymal stem cell attractant and a method for attracting a mesenchymal stem cell.

BACKGROUND ART

As the stem cells that can be differentiated into various tissue cells, embryonic stem cells (ES cells), which are the cells derived from the undifferentiated zygote, somatic stem cells, which are undifferentiated cells that are contained in differentiated tissues, and the like are known.

Somatic stem cells are present in a variety of tissues in the body, and examples thereof include mesenchymal stem cells present in the bone marrow.

Mesenchymal stem cells are undifferentiated cells that can be differentiated into cells belonging to mesenchymal tissues such as bone, muscle, and fat, and are known to be capable of differentiating also into ectodermal cells such as nerve cells and endodermal cells such as liver cells.

Also, mesenchymal stem cells have drawn attention for their ability to restore the function of a dysfunctional tissue by differentiating into the cells in such a tissue. Specifically, for example, bone marrow-derived mesenchymal stem cells have drawn attention for their potential to differentiate into the cells in inflamed tissues or damaged tissues under the influence of differentiation inducers, which induce differentiation, by being attracted to and accumulating in such tissues via the blood stream.

Meanwhile, conventionally, various substances are known as differentiation inducers that can differentiate mesenchymal stem cells into a variety of tissue cells. For example, substances containing PDGF-BB as the platelet-derived growth factor that can differentiate mesenchymal stem cells into muscle tissue cells are known (Patent Document 1).

CITATION LIST

Patent Document

Patent Document 1: International Publication No. WO 2005/063967

SUMMARY OF INVENTION

Technical Problem

However, the differentiation inducer of this kind has the following problem: although the inducer is capable of differentiating mesenchymal stem cells into specific tissue cells, its ability to attract mesenchymal stem cells, for example, to attract bone marrow-derived mesenchymal stem cells that are circulating within the body via the blood stream to a specific tissue in the body, is not necessarily satisfactory.

In view of the aforementioned problem and the like, the present invention aims to provide a mesenchymal stem cell attractant that can attract mesenchymal stem cells. Also, the present invention aims to provide a method for attracting a mesenchymal stem cell, which includes attracting a mesenchymal stem cell by the aforementioned attractant.

Solution to Problem

The mesenchymal stem cell attractant of the present invention is characterized by containing at least one selected from the group consisting of an extract of a *Bodhi* tree, an extract of the root bark of *Paeonia suffruticosa* Andrews, an extract of *Mallotus philippinensis*, an extract of *Uncaria gambir*, an extract of *Pashanbheda*, and an extract of a plant belonging to the genus *Prunus*.

The method for attracting a mesenchymal stem cell according to the present invention is characterized by attracting a mesenchymal stem cell by the aforementioned attractant.

Advantageous Effects of Invention

The mesenchymal stem cell attractant of the present invention has an effect of being capable of attracting a mesenchymal stem cell.

DESCRIPTION OF EMBODIMENTS

Figure 1:
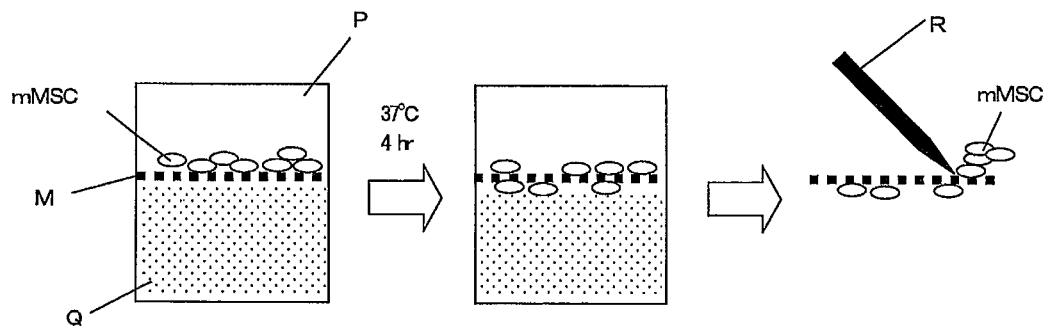
FIG. 1 is a diagram schematically illustrating the chemotaxis assay.
Figure 2:
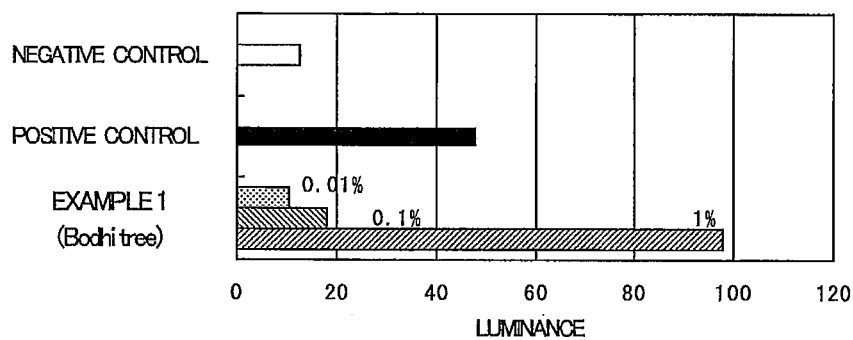
FIG. 2 is a graph showing the results of the chemotaxis assay using the attractant of Example 1.
Figure 3:
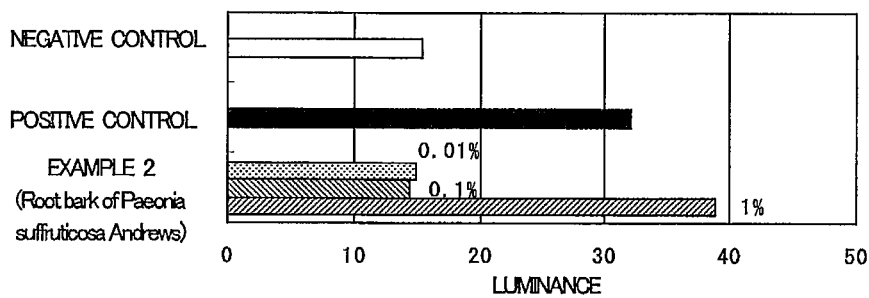
FIG. 3 is a graph showing the results of the chemotaxis assay using the attractant of Example 2.
Figure 4:
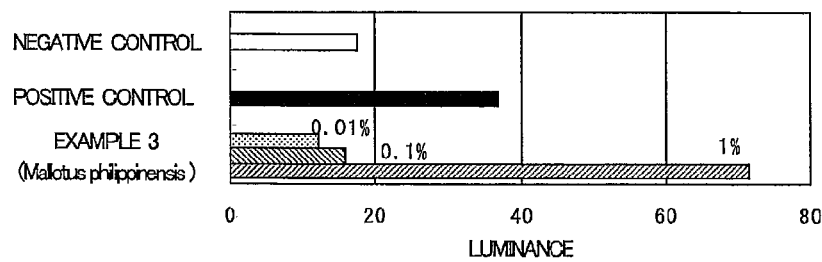
FIG. 4 is a graph showing the results of the chemotaxis assay using the attractant of Example 3.
Figure 5:
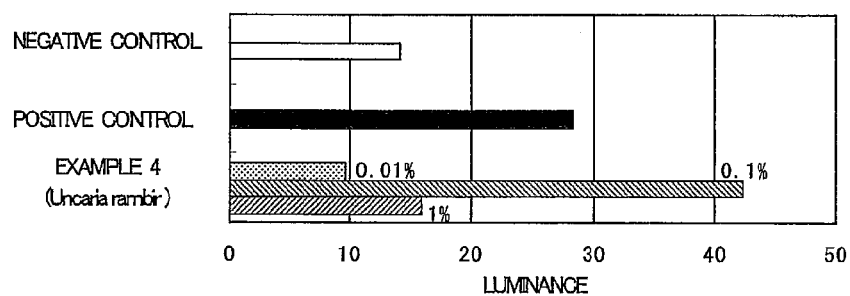
FIG. 5 is a graph showing the results of the chemotaxis assay using the attractant of Example 4.
Figure 6:
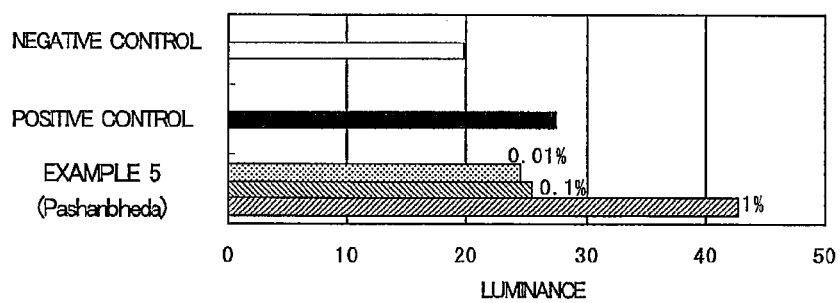
FIG. 6 is a graph showing the results of the chemotaxis assay using the attractant of Example 5.
Figure 7:
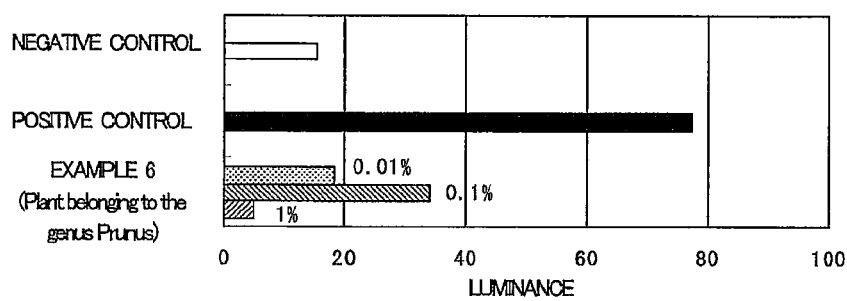
FIG. 7 is a graph showing the results of the chemotaxis assay using the attractant of Example 6.

Hereinafter, the embodiments of the mesenchymal stem cell attractant of the present invention will be described.

The mesenchymal stein cell attractant according to the present embodiments contains at least one selected from the group consisting of an extract of a *Bodhi* tree, an extract of the root bark of *Paeonia suffruticosa* Andrews, an extract of *Mallotus philippinensis*, an extract of *Uncaria gambir*, an extract of *Pashanbheda*, and an extract of a plant belonging to the genus *Prunus*.

The aforementioned extract of a *Bodhi* tree is obtained by extracting a plant belonging to the family Tiliaceae with an extraction solvent. Examples of the plant belonging to the family Tiliaceae include *Tilia platyphyllos* Scop., *Tilia cordata* Mill., and *Tilia europaea* L., or other plants closely related to these plants. Among them, as the plant belonging to the family Tiliaceae, *Tilia cordata* Mill. is preferable because it has better ability to attract mesenchymal stem cells. That is, as the aforementioned extract of a *Bodhi* tree, an extract of *Tilia cordata* Mill. is preferable.

The part of the aforementioned plant belonging to the family Tiliaceae that is subjected to extraction is not particularly limited, and examples of the part to be extracted include flowers, fruits, and bark. Among them, as the part to be extracted, flowers are preferable because they have better ability to attract mesenchymal stem cells.

The aforementioned extract of the root bark of *Paeonia suffruticosa* Andrews is obtained by extracting the root bark of *Paeonia suffruticosa* Andrews with an extraction solvent.

The aforementioned extract of *Mallotus philippinensis* is obtained by extracting *Mallotus philippinensis* belonging to the family Euphorbiaceae with an extraction solvent.

The part of the aforementioned *Mallotus philippinensis* that is subjected to extraction is not particularly limited, and examples of the part to be extracted include leaves, branches, trunks, bark, and roots. Among them, bark is preferable because it has better ability to attract mesenchymal stem cells.

The aforementioned extract of *Uncaria gambir* is obtained by extracting *Uncaria gambir* with an extraction solvent.

The part of the aforementioned *Uncaria gambir* that is subjected to extraction is not particularly limited, and examples of the part to be extracted include leaves and shoots. As the aforementioned extract of *Uncaria gambir*, the extract obtained by extracting both leaves and shoots with an extraction solvent is preferable because it has better ability to attract mesenchymal stem cells.

The aforementioned extract of *Pashanbheda* is obtained by extracting one or two or more of *Pashanbheda* belonging to the genus *Bergenia stracheyi* of the family Saxifragaceae with an extraction solvent. Examples of *Pashanbheda* include *Bergenia ligulata* (Wall.) Engl., *Bergenia stracheyi* (Hook. f. & Thorns) Engl., or *Bergenia ciliate* (Haw.) Sternb. Among them, an extract obtained by extracting *Bergenia ligulata* (Wall.) Engl. with an extraction solvent is preferable because it has better ability to attract mesenchymal stem cells.

The part of the aforementioned *Pashanbheda* that is subjected to extraction is not particularly limited; however, rhizomes are preferable because they have better ability to attract mesenchymal stem cells.

The aforementioned extract of a plant belonging to the genus *Prunus* is obtained by extracting a plant belonging to the genus *Prunus* of the family Roaceae with an extraction solvent. Examples of the plant belonging to the genus *Prunus* include *Prunus speciosa, Prunus jamasakura, Prunus sargentii, Prunus spachiana, Prunus incisa, Prunus maximowiczii, Prunus×yedoensis, Prunus nipponica, Prunus leveilleana, Prunus apetala, Prunus* sub. hirtella, *Prunus lannesiana*, and *Prunus kanzakura*, all belonging to the subgenus *Cerasus*. Among them, as the plant belonging to the genus *Prunus, Prunus xyedoensis* is preferable because it has better ability to attract mesenchymal stein cells. That is, as the aforementioned extract of a plant belonging to the genus *Prunus*, an extract of *Prunus×yedoensis* is preferable.

The part of the plant belonging to the genus *Prunus* that is subjected to extraction is not particularly limited, and examples of the part to be extracted include flowers, roots, leaves, fruits, and seeds. Among them, leaves are preferable because they have better ability to attract mesenchymal stem cells.

One of the aforementioned extracts can be used alone, or a mixture of two or more thereof can be used as the aforementioned mesenchymal stem cell attractant.

Each of the aforementioned plant extracts can normally be in the form of an extraction liquid obtained using the aforementioned extraction solvent, a diluted solution of the extract, a concentrate of the extract, or a dried product obtained by removing the extraction solvent contained in the extract. Specifically, each extract can be in the form of, for example, a solution, a paste, a gel, and a powder.

Examples of the aforementioned extraction solvent include water or an organic solvent such as an aliphatic monovalent alcohol such as methanol, ethanol, and propanol; an aliphatic polyvalent alcohol such as glycerin, propylene glycol, and 1,3-butylene glycol; ketones such as acetone; diethyl ether, dioxane, acetonitrile, and esters such as acetic acid ethyl ester; aromatic compounds such as xylene, benzene, and toluene; and halogenated alkyls such as chloroform.

One of the above extraction solvents can be used alone or a mixture of two or more thereof can be used. The mixing ratio in the mixture of the extraction solvents is not particularly limited and is appropriately adjusted.

As the aforementioned extraction solvent, a hydrous extraction solvent containing at least water is preferable. Also, as the aforementioned extraction solvent, an extraction solvent containing an aliphatic alcohol such as an aliphatic monovalent alcohol or an aliphatic polyvalent alcohol and water is more preferable, and an extraction solvent containing an aliphatic monovalent alcohol and water is even more preferable, and an extraction solvent containing water and ethanol is most preferable in view of better ability to attract mesenchymal stem cells.

As the aforementioned extraction solvent, specifically, for example, an extraction solvent in which an aliphatic alcohol such as an aliphatic monovalent alcohol or an aliphatic polyvalent alcohol and water are mixed at a volume ratio of an aliphatic alcohol:water=7:3 to 3:7 is preferable.

More specifically, as the aforementioned extraction solvent, an extraction solvent in which ethanol and water are mixed at a volume ratio of ethanol:water=7:3 to 3:7 is preferable.

The method of the aforementioned extraction is not particularly limited, and a conventionally known, general extraction method can be adopted. In extraction, the part of each plant to be extracted can be used directly or after drying as the extraction raw material. Also, normally, the amount of extraction solvent is five to fifteen times (weight ratio) as much as the amount of extraction raw material, and the extraction temperature is 20° C. to 80° C. and the extraction time is two hours to three days. After extraction, purification treatment such as filtration, deodorization, and bleaching can be appropriately performed as needed.

The concentration of each of the aforementioned extracts contained in the aforementioned mesenchymal stem cell attractant is not particularly limited. For example, the concentration is 0.1 to 5.0% by weight in terms of dry weight.

It is to be noted that the phrase "in terms of dry weight" refers to converting the amount of extract into the weight of its dried form, which is the residue obtained after removing the extraction solvent from the extract.

Next, the embodiments of the method for attracting a mesenchymal stem cell according to the present invention will be described. The method for attracting a mesenchymal stem cell according to the present embodiments is to attract a mesenchymal stem cell by the aforementioned mesenchymal stem cell attractant.

Mesenchymal stem cells are found in the mesenchymal tissue cells, and they can differentiate not only into the cells of mesodermal tissues such as cartilage, fat, and muscle, but also into the cells of ectodermal tissues such as nerves and the cells of endodermal tissues such as liver. Also, as the mesenchymal stem cells to be attracted, bone marrow mesenchymal stem cells are preferable because they can be comparatively easily collected from the bone marrow and it has already been recognized that they can also be present in blood.

According to the aforementioned method for attracting a mesenchymal stem cell, mesenchymal stem cells can be attracted by the aforementioned mesenchymal stein cell attractant in vitro, in vivo, or in situ.

Specifically, for example, as the method for attracting a mesenchymal stem cell in vitro, methods such as a method in which, using an apparatus having a membrane having micropores that penetrate in the direction of thickness, mesenchymal stem cells are placed in one side of the membrane and the aforementioned mesenchymal stem cell attractant is placed in the other side of the membrane, whereby the mesenchymal stem cells are attracted to the other side of the membrane over a certain period of time can be performed.

Also, for example, as the method for attracting a mesenchymal stem cell in vitro, methods such as a method in which the mesenchymal cells inoculated onto a slide glass are partially scraped off, and to the scraped area, a medium containing the aforementioned mesenchymal stem cell attractant is added for culturing, whereby the mesenchymal stem cells are attracted to the scraped area can be performed. The degree of attraction of bone marrow mesenchymal stem cells can be evaluated by confirming the movement of mesenchymal stem cells in the scraped area.

Also, for example, as the method for attracting a mesenchymal stem cell in vivo, methods such as a method in which an aqueous gel containing the aforementioned mesenchymal stem cell attractant is subcutaneously implanted in mice, and into these mice, mouse bone marrow mesenchymal stem cells expressing Green Fluorescent Protein (hereinafter, sometimes referred to as GFP) are intravenously injected, and the mice are reared for a certain period of time, whereby the bone marrow mesenchymal stem cells are attracted to the gel can be performed. The degree of attraction of bone marrow mesenchymal stem cells can be evaluated by measuring the fluorescent intensity in the gel.

Also, for example, as the method for attracting a mesenchymal stem cell in vivo, methods such as a method in which mouse bone marrow mesenchymal stem cells expressing GFP are transplanted into the bone marrow of injury model mice, and at the same time, the aforementioned mesenchymal stein cell attractant is applied to the injury site in the mice, whereby the bone marrow mesenchymal stein cells derived from the GFP mice are attracted to the injury site can be performed. The degree of attraction of bone marrow mesenchymal stem cells can be evaluated by measuring the fluorescent intensity in the injury site.

Also, for example, as the method for attracting a mesenchymal stein cell in situ, methods such as a method in which the mesenchymal stem cell attractant is applied to a specific tissue, whereby bone marrow mesenchymal stem cells are attracted to the tissue can be performed. More specifically, for example, methods such as a method in which the mesenchymal stem cell attractant is applied to the skin epidermal tissue, whereby bone marrow mesenchymal stem cells present in blood are attracted to the epidermal tissue can be performed.

The aforementioned methods for attracting a mesenchymal stem cell can be applied to animals other than humans in situ. Also, these methods can be non-therapeutically applied to humans.

Also, examples of the specific tissue in the in situ method of attraction include not only the aforementioned epidermal tissue, but also a variety of tissues such as a muscle tissue, a cartilage tissue, and a liver tissue.

In the aforementioned methods for attracting a mesenchymal stem cell, the aforementioned mesenchymal stem cell attractant can be used after dilution. Solutions used for dilution are not particularly limited, and for example, water, physiological saline, and a culture medium for mesenchymal cells can be used. No particular limitation is imposed on the concentration of the extract in the diluted solution obtained by diluting the mesenchymal stem cell attractant when the attractant is used; however, the concentration is preferably 0.00001 to 0.05% by weight in terms of dry weight. It is advantageous that the concentration of the extract is 0.00001% by weight or more in terms of dry weight because that way excellent ability to further attract a mesenchymal stem cell is achieved. Also, the concentration of the extract is preferably 0.05% by weight or less because the toxicity to mesenchymal stem cells can be further reduced.

Specifically, in the aforementioned methods for attracting the mesenchymal stem cell, the attractant containing an extract of a *Bodhi* tree is used preferably at a concentration of 0.00001 to 0.01% by weight, more preferably at a concentration of 0.0001 to 0.01% by weight in terms of dry weight.

Also, the attractant containing an extract of the root bark of *Paeonia suffruticosa* Andrews is used preferably at a concentration of 0.00001 to 0.01% by weight, more preferably at a concentration of 0.0001 to 0.01% by weight in terms of dry weight.

Also, the attractant containing an extract of *Mallotus philippinensis* is used preferably at a concentration of 0.00001 to 0.01% by weight, more preferably at a concentration of 0.0001 to 0.01% by weight in terms of dry weight.

Also, the attractant containing an extract of *Uncaria gambir* is used preferably at a concentration of 0.0001 to 0.05% by weight, more preferably at a concentration of 0.001 to 0.01% by weight in terms of dry weight.

Also, the attractant containing an extract of *Pashanbheda* is used preferably at a concentration of 0.00001 to 0.01% by weight, more preferably at a concentration of 0.0001 to 0.01% by weight in terms of dry weight.

Also, the attractant containing an extract of a plant belonging to the genus *Prunus* such as an extract of *Prunus xyedoensis* is used preferably at a concentration of 0.0001 to 0.05% by weight, more preferably at a concentration of 0.001 to 0.01% by weight in terms of dry weight.

The mesenchymal stem cell attractant and the method for attracting a mesenchymal stem cell according to the present embodiments are illustrated as above; however, the present invention is not limited to the mesenchymal stem cell attractant and the method for attracting a mesenchymal stem cell exemplified as above. Also, in the present invention, various embodiments adopted for general mesenchymal stem cell attractants and methods for attracting a mesenchymal stem cell can be adopted so long as the effect of the present invention is not impaired.

EXAMPLES

Next, the present invention will be described in further detail with reference to Examples; however, the present invention is not limited to these Examples.

First of all, as will be shown below, the mesenchymal stem cell attractants composed of only respective extracts were produced by preparing respective extracts. The detail of the production will be described.

Example 1

As the extract of a *Bodhi* tree of Example 1, an extraction liquid of *Tilia cordata* Mill. was prepared. In detail, to 100 g of finely crushed dried flowers of *Tilia cordata* Mill., 1 L of a 50% by volume aqueous solution of ethanol was added, and extraction operation was performed at room temperature (20° C.) for three days, followed by filtration treatment. Further, the filtrate was dried under reduced pressure to give a dried product, which was diluted with 1,3-butylene glycol to prepare an extraction liquid of *Tilia cordata* Mill. The resulting extraction liquid of a *Bodhi* tree was found to contain 0.45% by weight of dried product according to the calculation from the dry weight after removing the extraction solvent by drying under reduced pressure.

Example 2

As the extract of the root bark of *Paeonia suffruticosa* Andrews of Example 2, an extraction liquid of the root bark of *Paeonia suffruticosa* Andrews was prepared. In detail, to 100 g of finely crushed dried root bark of *Paeonia suffruticosa* Andrews, 1 L of a 50% by volume aqueous solution of ethanol was added, and extraction operation was performed at room temperature (20° C.) for three days, followed by filtration treatment. Further, the filtrate was dried under reduced pressure to give a dried product, which was diluted with 1,3-butylene glycol to prepare an extraction liquid of the root bark of *Paeonia suffruticosa* Andrews. The resulting extraction liquid of the root bark of *Paeonia suffruticosa* Andrews was found to contain 0.90% by weight of dried product according to the calculation from the dry weight after removing the extraction solvent by drying under reduced pressure.

Example 3

As the extract of *Mallotus philippinensis* of Example 3, an extraction liquid of *Mallotus philippinensis* was prepared. In detail, to 200 g of finely crushed dried bark of *Mallotus philippinensis* Mueller-Argoviensis, 2 L of a 50% by volume aqueous solution of ethanol was added, and extraction operation was performed for two days while maintaining the temperature at 60 to 80° C., followed by filtration treatment. Further, the filtrate was dried under reduced pressure to give a dried product, which was diluted with 1,3-butylene glycol to prepare an extraction liquid of *Mallotus philippinensis*. The resulting extraction liquid of *Mallotus philippinensis* was found to contain 0.20% by weight of dried product according to the calculation from the dry weight after removing the extraction solvent by drying under reduced pressure.

Example 4

As the extract of *Uncaria gambir* of Example 4, an extraction liquid of *Uncaria gambir* was prepared. In detail, to 100 g of finely crushed dried leaves and shoots of *Uncaria gambir* Roxburgh, 2 L of a 50% by volume aqueous solution of ethanol was added, and extraction operation was performed for three hours, while maintaining the temperature at 50 to 70° C. while stirring, followed by filtration treatment. Further, the filtrate was dried under reduced pressure to give a dried product, which was diluted with 1,3-butylene glycol to prepare an extraction liquid of *Uncaria gambir*. The resulting extraction liquid of *Uncaria gambir* was found to contain 4.10% by weight of dried product according to the calculation from the dry weight after removing the extraction solvent by drying under reduced pressure.

Example 5

As the extract of *Pashanbheda* of Example 5, an extraction liquid of Pashanbheda was prepared. In detail, to 200 g of finely crushed dried rhizomes of *Bergenia ligulata* (Wall.) Engl., 3 Kg of a 50% by volume aqueous solution of ethanol was added, and extraction operation was performed at 50° C. for eight hours while stirring. The crude extract was cooled, filtered, concentrated, and treated with a column filled with synthetic adsorbents (trade name "Diaion HP-20", the product of Mitsubishi Chemical Corporation). Subsequently, the column was washed with water and eluted with a 30% by volume aqueous solution of ethanol. The eluent thus obtained was dried under reduced pressure, and the residue was dissolved again in 1,3-butylene glycol to prepare an extraction liquid of *Pashanbheda*. The resulting extraction liquid of *Pashanbheda* was found to contain 0.50% by weight of dried product according to the calculation from the dry weight after removing the extraction solvent by drying under reduced pressure.

Example 6

As the extract of the plant belonging to the genus *Prunus* of Example 6, an extraction liquid of *Prunus×yedoensis* was prepared. In detail, to 100 g of finely crushed dried leaves of *Prunus×yedoensis*, 1 L of a 50% by volume aqueous solution of ethanol was added, and extraction operation was performed at room temperature (20° C.) for three days while stirring, followed by filtration treatment. Further, the filtrate was dried under reduced pressure to give a dried product, which was diluted with 1,3-butylene glycol to prepare an extraction liquid of *Prunus×yedoensis*. The resulting extraction liquid of *Prunus×yedoensis* was found to contain 2.00% by weight of dried product according to the calculation from the dry weight after removing the extraction solvent by drying under reduced pressure.

Subsequently, each of the extracts thus prepared was used as the mesenchymal stem cell attractant and evaluated by a chemotaxis assay. FIG. 1 is a diagram schematically illustrating the evaluation method. Hereinafter, the detail of the evaluation method will be described with reference to FIG. 1.

<Chemotaxis Assay (Cell Attracting Test)>

The extracts produced in respective Examples were diluted to 0.01% by volume, 0.1% by volume, or 1% by volume to prepare test samples. For dilution, Dulbecco's modified eagle's medium [DMEM "FBS(−), P/S(−)"] was used. Here, FBS in the square brackets indicates 10% fetal bovine serum and P/S indicates 100 units penicillin and 0.1 mg/mL streptomycin. Also, the symbol (−) indicates that the indicated substance is not added.

Meanwhile, as the negative control sample (hereinafter, sometimes referred to as N.C.), DMEM "FBS(−), P/S(−)" was prepared, and as the positive control sample (hereinafter, sometimes referred to as P.C.), 20 ng/mL PDGF-BB (platelet-derived growth factor, the product of Pepro Tech, Ltd.) was prepared.

Also, mouse bone marrow mesenchymal stem cells (hereinafter, sometimes referred to as mMSC) were cultured to confluence and harvested, and then suspended in 10% FBS/DMEM [P/S (−)] at $1×10^7$ cells/ml, whereby cell suspensions were prepared.

Subsequently, Boyden chambers (the product of Neuro Probe, Inc.) having a plurality of independent wells, in which the upper well (P) and the lower well (Q) are separated by the membrane M as shown in FIG. 1(a), were prepared. The chambers were set so that any one of the test samples, the negative control sample, and the positive control sample were tested in the same Boyden chamber, and each sample was applied to each lower well of the chamber in an amount of 28 μl. It is to be noted that as the membrane of the Boyden chamber, the trade name "Polycarbonate Membranes" (the product of Neuro Probe, Inc., pore size 8 μm) was adopted.

Subsequently, in the upper wells P of the Boyden chambers, the aforementioned cell suspensions were inoculated in an amount of 50 μl each, and then cultured for four hours under the conditions of 37° C. and 5% $CO_2$ (see FIG. 1(b)).

After four hours of culture, as shown in FIG. 1(c), mMSC that did not migrate was scraped off by the attached filter wiper R, and only mMSC that had migrated to below the membrane was stained with DIFF-QUIK® stain (using the kit manufactured by Sysmex Corporation).

Subsequently, the stained image was digitized and fed into a computer, and in order to binarize the image into black and white, the image was converted so that the part that was stained blue appeared in white. Then, an average value of luminance within each well was measured using the function of an image editing software (the trade name "PHOTO-SHOP®"). By comparing the luminance of the negative and positive control samples with that of each test sample, the mMSC-attracting activity of the mesenchymal stem cell attractant produced in each Example was evaluated.

The evaluation results of Examples 1 to 6 are each shown in FIGS. 2 to 7.

Figure 8:
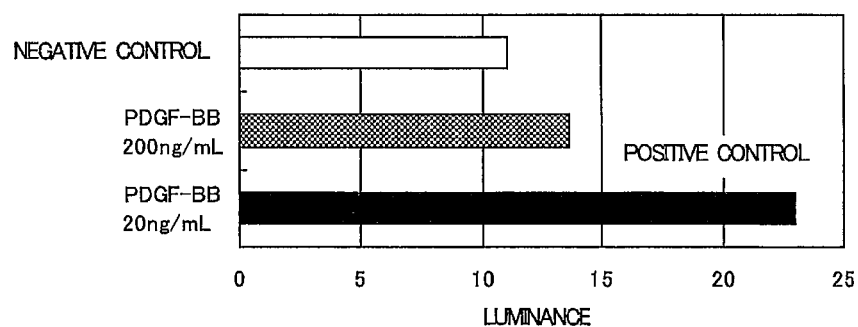
FIG. 8 is a graph showing the results of the chemotaxis assay using the negative control and the positive control.

Also, as a referential experiment, a chemotaxis assay was performed in a similar manner to the above by changing the concentration of PDGF-BB used as the positive control sample. The results thus obtained are shown in FIG. 8.

INDUSTRIAL APPLICABILITY

The mesenchymal stem cell attractant and method for attracting a mesenchymal stem cell according to the present invention can be suitably used for, for example, evaluating a difference in the ability of each mesenchymal stem cell in various tissues to accumulate (to be attracted) via migration.

Also, the mesenchymal stem cell attractant and method for attracting a mesenchymal stem cell according to the present invention can be suitably used in, for example, methods such as a method in which the attractant is applied to a tissue in the body by, for example, injecting or applying it to a specific tissue in the body, whereby mesenchymal stem cells in blood that are circulating in the body via the blood stream are attracted to and accumulated in the specific tissue so that the mesenchymal stem cells are, in the tissue, differentiated into the specific tissue.

REFERENCE SIGNS LIST

P: Upper well, Q: Lower well, M: Membrane, and R: Filter wiper

The invention claimed is:

1. A method for treating an injury to skin tissue, muscle tissue, cartilage tissue or liver tissue of a subject, comprising enhancing the migratory capacity of mesenchymal stem cells in the blood of the subject whereby to attract the mesenchymal stem cells to the injury site to thereby reduce injury healing time by determining the site of injury to said tissue then applying an effective amount of a mesenchymal stem cell attractant comprising an extract of *Mallotus philippinensis* to the injury site.

2. The method according to claim 1, wherein the mesenchymal stem cell attractant is applied to epidermal skin tissue.

3. The method according to claim 1, wherein the mesenchymal stem cell attractant is applied to the skin tissue, the muscle tissue, the cartilage tissue or the liver tissue of humans.

4. The method according to claim 1, wherein the mesenchymal stem cell attractant is applied to human skin.

5. The method according to claim 4, wherein the mesenchymal stem cell attractant is applied to human epidermal skin tissue.

6. The method according w claim 1, wherein the mesenchymal stem cell attractant is applied to the skin tissue, the muscle tissue, the cartilage tissue or the liver tissue of animals other than humans.

7. A method for treating an injury to muscle tissue of a subject, comprising determining the site of injury to said tissue then applying an effective amount of a mesenchymal stem cell attractant comprising an extract of *Mallotus philippinensis* to the injury site whereby to attract mesenchvmal stem cells in the blood of the subject to the injury site.

8. A method for treating an injury to cartilage tissue of a subject, comprising determining the site of injury to said tissue then applying an effective amount of a mesenchymal stem cell attractant comprising an extract of *Mallotus philippinensis* to the injury site whereby to attract mesenchymal stem cells in the blood of the subject to the injury site.

9. A method for treating an injury to liver tissue of a subject, comprising determining the site of injury to said tissue then applying an effective amount of a mesenchymal stem cell attractant comprising an extract of *Mallotus philippinensis* to the injury site whereby to attract mesenchymal stem cells in the blood of the subject to the injury site.

* * * * *